United States Patent
Grossmann et al.

(10) Patent No.: US 12,012,581 B2
(45) Date of Patent: Jun. 18, 2024

(54) METHOD AND SYSTEM FOR HETEROTROPHIC AND MIXOTROPHIC CULTIVATION OF MICROALGAE

(71) Applicant: GICON Grossmann Ingenieur Consult GmbH, Dresden (DE)

(72) Inventors: Jochen Grossmann, Dresden (DE); Fritz Cotta, Wolfen (DE); Martin Ecke, Klötze (DE)

(73) Assignee: GICON Grossmann Ingenieur Consult GmbH, Dresden (DE)

( * ) Notice: Subject to any disclaimer, the term of this patent is extended or adjusted under 35 U.S.C. 154(b) by 608 days.

(21) Appl. No.: 16/649,995

(22) PCT Filed: Oct. 8, 2018

(86) PCT No.: PCT/EP2018/077264
§ 371 (c)(1),
(2) Date: Mar. 24, 2020

(87) PCT Pub. No.: WO2019/072738
PCT Pub. Date: Apr. 18, 2019

(65) Prior Publication Data
US 2020/0231923 A1  Jul. 23, 2020

(30) Foreign Application Priority Data
Oct. 10, 2017  (DE) .......................... 102017218001.3

(51) Int. Cl.
*C12M 1/00* (2006.01)
*C12M 1/12* (2006.01)

(52) U.S. Cl.
CPC ............ *C12M 29/18* (2013.01); *C12M 21/02* (2013.01); *C12M 23/06* (2013.01); *C12M 23/22* (2013.01); *C12M 31/02* (2013.01)

(58) Field of Classification Search
CPC .................................................... C12M 21/02
See application file for complete search history.

(56) References Cited

U.S. PATENT DOCUMENTS 5,081,035 A * 1/1992 Halberstadt ............ C12M 23/24
                                                           210/321.79
2015/0232802 A1   8/2015 Ganuza et al.
(Continued)

FOREIGN PATENT DOCUMENTS

CN     104789631 A      7/2015
DE   102008059562 A1    7/2009
(Continued)

OTHER PUBLICATIONS

Ogbonna James E et al.: "Light requirement and photosynthetic cell cultivation: Development of processes for efficient light utilization in photobioreactors", Oct. 1, 2000 (Oct. 1, 2000), Journal of Applied Phycology, Kluwer, Dordrecht, NL, pp. 207-2018, XP002473562, ISSN: 0921-8971; mentioned in the application, p. 212-p. 215; Fig. 5.
(Continued)

*Primary Examiner* — Jonathan M Hurst
(74) *Attorney, Agent, or Firm* — Heslin Rothenberg Farley & Mesiti P.C.

(57) ABSTRACT

The invention relates to a method for the simultaneous heterotrophic and mixotrophic cultivation of microalgae, to a system for the simultaneous heterotrophic and mixotrophic cultivation of microalgae and to the use of the method and/or the system for the cultivation of microalgae.

19 Claims, 1 Drawing Sheet

(56) References Cited

U.S. PATENT DOCUMENTS

| | | |
|---|---|---|
| 2016/0115432 A1 | 4/2016 | Dahiya |
| 2016/0145668 A1 | 5/2016 | Garnier et al. |
| 2017/0218319 A1 | 8/2017 | Dahiya |

FOREIGN PATENT DOCUMENTS

| | | | | |
|---|---|---|---|---|
| DE | 102009045851 A1 | 4/2011 | | |
| EP | 2316917 A1 | 5/2011 | | |
| WO | WO-2012074502 A1 * | 6/2012 | ............... | A01H 3/00 |
| WO | WO-2012109375 A2 * | 8/2012 | ............. | A01G 33/00 |
| WO | WO-2013048543 A1 * | 4/2013 | ............. | A01G 33/00 |
| WO | 2014074772 A1 | 5/2014 | | |
| WO | 2014144270 A1 | 9/2014 | | |

OTHER PUBLICATIONS

James C Ogbonna et al.: "Sequential heterotrophic/autotrophic cultivation—An efficient method of producing Chlorella, biomass for health food and animal feed", Jul. 1, 1997 (Jul. 1, 1997), Journal of Applied Phycology, Kluwer Academic Publishers, DO, pp. 359-366, XP019247857, ISSN: 1573-5176; The whole document.
Lee Yuan-Kun: "Microalgal mass culture systems and methods: Their limitation and potential", Aug. 2001, Journal of Applied Phycology 13, pp. 307-315.

* cited by examiner

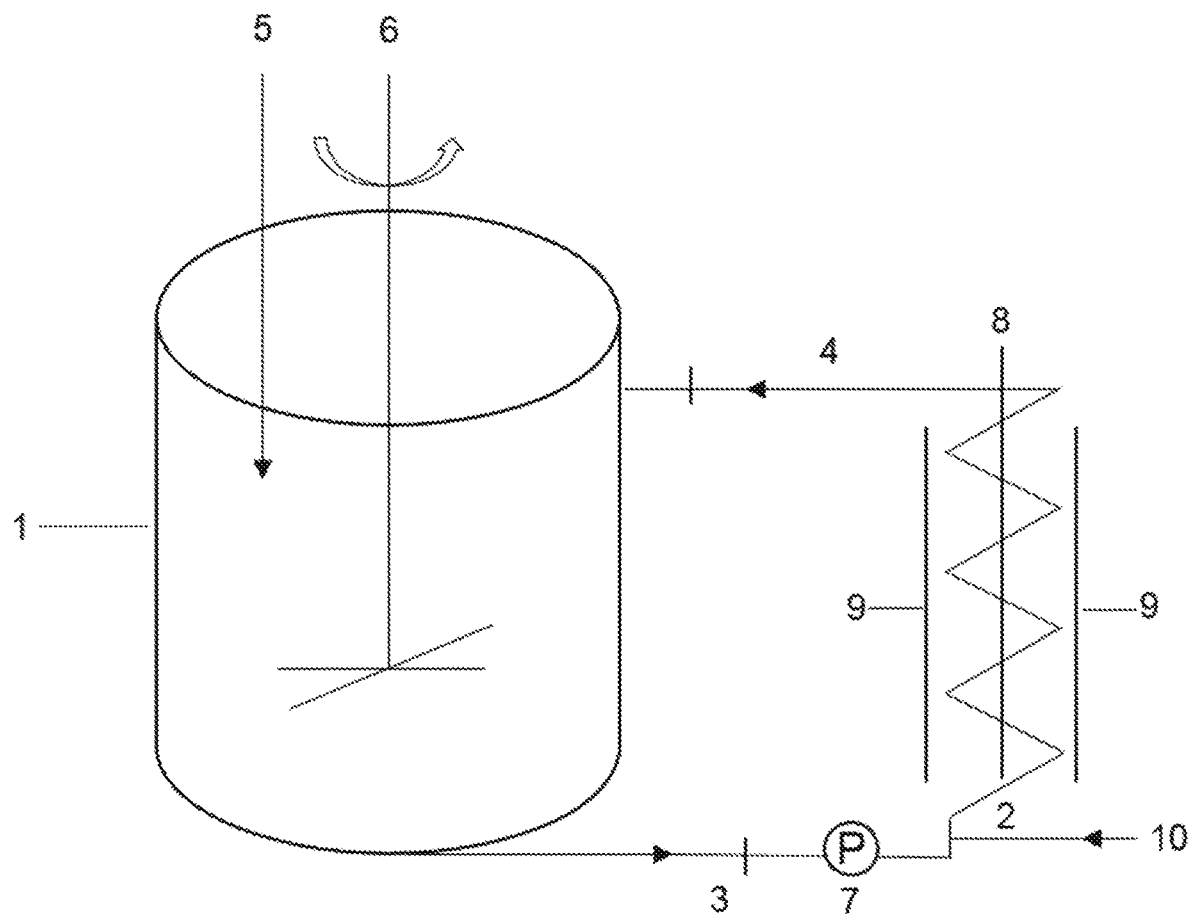

METHOD AND SYSTEM FOR HETEROTROPHIC AND MIXOTROPHIC CULTIVATION OF MICROALGAE

CROSS REFERENCE TO RELATED APPLICATIONS

This application is the U.S. national stage of International Application No. PCT/EP2018/077264, filed on 2018 Oct. 8. The international application claims the priority of DE 102017218001.3 filed on 2017 Oct. 10; all applications are incorporated by reference herein in their entirety.

BACKGROUND

The invention relates to a method for the simultaneous heterotrophic and mixotrophic cultivation of microalgae, to a system for the simultaneous heterotrophic and mixotrophic cultivation of microalgae and to the use of the method and/or the system for the cultivation of microalgae.

Microalgae are a valuable resource for the production of food and feed, fine chemicals, pharmaceuticals and cosmetic products because they are able to grow organic substances from the carbon dioxide contained in the air and essential mineral nutrients in the presence of light while releasing oxygen. This process is called phototrophy.

A considerable number of microalgae are still able to grow organic biomass from suitable organic substrates and essential mineral nutrients in the presence of oxygen, even in the absence of light, using the chemical energy stored in the organic substrates. This process is called heterotrophy. Some of these microalgae can act simultaneously phototrophically and heterotrophically. This form is called mixotrophy.

A prerequisite for phototrophic cultivation on an industrially relevant scale is the sufficient availability of inorganic carbon in the cultivation system. The addition of inorganic carbon takes place mainly by introducing gaseous carbon dioxide or hydrogen carbonate into the culture medium. Another prerequisite for phototrophic cultivation is the provision of the required light intensities in the culture suspension by structural measures, in particular by guiding the culture medium in layers that are as thin as possible, as well as the highest possible turbulence within the cultures in order to ensure the necessary nutrient supply, gas exchange and light availability in dense cultures.

Two different forms of cultivation systems have become established for the phototrophic cultivation of microalgae on an industrial scale (Lee 2001). One form is the cultivation of microalgae in open devices. Installations in which the microalgae to be cultivated are in direct contact with the environment in order to ensure the light input required for the cultivation process are referred to as open devices or open systems. Open devices for microalgae cultivation may be natural lakes, pools, basins ("ponds") and artificial river courses ("raceway ponds"), in which the microalgae are cultivated by carbon dioxide being supplied from the air or by directly feeding carbon dioxide or carbon dioxide mixtures into the aqueous culture medium containing the required mineral nutrients. Alternatively, hydrogen carbonate can also act as a carbon source for certain types of algae within the appropriate pH ranges. The required gas exchange, including the discharge of the oxygen formed during photosynthesis, takes place on the surface of the water in direct contact with the ambient air. The medium can be thoroughly mixed by wind, blowing in air, by agitators or by circulating the medium by pumping. In most cases, the depth of the water is less than 30 cm to ensure the required light input, in particular by sunlight. Open systems can also be provided with transparent covers to reduce the effects of weather and the input of pollutants.

Drawbacks of open systems are high susceptibility to contamination of a microbial and chemical nature, high water losses due to evaporation, low photosynthesis efficiency due to the low atmospheric carbon dioxide partial pressure as well as low biomass densities, in particular less than 1 g/l, and low space/time yields.

In selected cases, open systems can also be operated mixotrophically. Such methods are limited to a few, very fast growing algae species preferring a hypertrophic environment, e.g. representatives from the *Chlorella* cluster which also tolerate the accompanying bacteria inherent in these processes. In such methods, acetate preferably acts as the organic carbon source. The range of applications of mixotrophic processes in open systems is low due to the drastically increased risk of microbial contamination owing to the addition of organic nutrients. Products from such methods have to be purified and pasteurised in a complex process.

Another form of phototrophic cultivation of microalgae is cultivation in closed devices, also called photobioreactors (PBR). Devices in which the culture medium containing the microalgae is located in transparent reaction chambers so as to be shielded from the environment are referred to as photobioreactors. Tubular or cuboid devices as well as systems based on tubular bags are preferably used. Glass and various transparent polymers such as polyvinyl chloride (PVC), polyacrylate, polyethylene or silicone (DE 102009045851 A1) are used as preferred materials for the devices. In closed devices, the carbon dioxide required for photosynthesis is fed in and the oxygen released during photosynthesis is discharged, higher carbon dioxide partial pressures and thus higher biomass densities and higher productivity being achieved than in open systems. In order to optimise the light yield and increase the space/time yields, the layer thickness of the culture medium is kept low and the required turbulence is generated by pumping the suspension around or introducing process gases. The risk of contamination from xenobiotics is advantageously reduced by means of closed systems compared with open systems, with the risk of microbiological contamination being only marginally lower due to the non-sterile manner of operation which is standard in large-scale installations.

Closed systems are still used for mixotrophic or heterotrophic cultivation, with tanks or conventional fermenter systems being used for heterotrophic cultivation. Sterile process control is a prerequisite for large-volume heterotrophic cultivation. For heterotrophic cultivation with the addition of oxygen and a carbon source, in particular an organic carbon source, preferably glucose, higher biomass densities are advantageously obtained in the culture suspension. Disadvantageously, the composition of heterotrophically produced microalgae biomass differs from phototrophically produced microalgae biomass, with some economically attractive ingredients, e.g. vitamins and carotenoids, only being formed in phototrophic cultivation.

The combination of heterotrophic and phototrophic cultivation of dual-trophy-capable microalgae provides a possible alternative. DE 10 2008 059 562 A1 discloses a cultivation method for heterotrophic microalgae comprising heterotrophic cultivation and the cultivation in a photobioreactor under autotrophic or mixotrophic conditions, preferably under autotrophic conditions.

Ogbonna and Tanaka describe the need for light and the efficient use of light in photobioreactors, in particular through a combination of heterotrophic and phototrophic cultivation or sequential or cyclic heterotrophic/phototrophic cultivation (Ogbonna and Tanaka 2000). In addition to separately operated photoautotrophic and photoheterotrophic, that is to say mixotrophic, cultivation processes, the document discloses a sequential heterotrophic/photoautotrophic cultivation in which, after heterotrophic cultivation has taken place, the process is continued in a separate cultivation unit under photoautotrophic conditions until the desired products are formed. Furthermore, a variant, known as cyclic process control, for microalgae cultivation is disclosed, which is based on periodically successive heterotrophic and photoautotrophic method steps.

Furthermore, Ogbonna et al. discloses the sequential heterotrophic/phototrophic cultivation of *Chlorella* using fermenters and tubular photobioreactors or internally illuminated photobioreactors, an increase in the protein and chlorophyll content being achieved (Ogbonna et al. 1997). The transition from heterotrophic to phototrophic cultivation takes place after the organic carbon source has been completely consumed in order to suppress microbiological contamination.

The combination of heterotrophic and phototrophic cultivation in a device under the influence of light and in the presence of an organic carbon source leads to mixotrophic assimilation, with advantageously only phototrophically accessible ingredients otherwise being formed without unproductive adaptation times occurring during the transition to the other form of cultivation. A prerequisite for mixotrophic assimilation is an adequate supply of light in the low-light conditions required for mixotrophic processes, which is why only low biomass densities can be used.

SUMMARY

The invention relates to a method for the simultaneous heterotrophic and mixotrophic cultivation of microalgae, to a system for the simultaneous heterotrophic and mixotrophic cultivation of microalgae and to the use of the method and/or the system for the cultivation of microalgae.

DETAILED DESCRIPTION

The problem addressed by the present invention is therefore to combine methods for the heterotrophic and mixotrophic cultivation of microalgae with one another while avoiding the drawbacks described above.

Furthermore, the problem addressed by the invention is to provide a method for cultivating microalgae with high biomass densities and high space/time yields.

According to the invention, the problem is solved by the method according to the invention for the simultaneous heterotrophic and mixotrophic cultivation of microalgae, comprising the steps of a) providing an inoculum comprising at least one microalgae strain and inoculating a culture medium with the inoculum, b) cultivating the at least one microalgae strain in a first device under heterotrophic culture conditions, c) cultivating the at least one microalgae strain in a second device under mixotrophic culture conditions, wherein at least a portion of the at least one microalgae strain is conveyed from the first device in step b) to the second device in step c) and/or from the second device in step c) to the first device in step b), wherein a process gas is introduced at the lower end of the second device, wherein the process gas is introduced so as to be at least partially compressed or at least partially condensed.

Advantageously, the method according to the invention for the cultivation of microalgae enables high biomass densities and high space/time yields. Also advantageously, the microalgae, cultivated by the method according to the invention, form ingredients which are only formed in phototrophic cultivation. Also advantageously, the microalgae cultivated by means of the method according to the invention can be used without further adaptation phases for subsequent, in particular heterotrophic, phototrophic or mixotrophic method steps, or can be subjected to direct further processing.

According to the invention, "simultaneous heterotrophic and mixotrophic cultivation of microalgae" is the simultaneous heterotrophic cultivation after step b) and mixotrophic cultivation after step c) of at least a portion of the at least one microalgae strain. The simultaneous heterotrophic and mixotrophic cultivation of microalgae preferably takes place in separate regions of a reactor system, in particular in a first and a second device, which are permanently interconnected by at least one connecting element.

According to the invention, "heterotrophic cultivation" means cultivation in the presence of organic substrates, essential mineral nutrients, and oxygen. The heterotrophic cultivation advantageously makes it possible to provide high concentrations of microalgae.

"Organic substrates" are understood to be organic carbon sources. In one embodiment, organic substrates are selected from glucose, acetic acid, acetates, lactates, ethanol, urea and/or glutamate. In another embodiment, organic substrates are selected from filtered and sterilised, liquid fermentation residues from biogas production, hydrolysates from starch-containing raw materials, preferably potato or maize slop or yeast extracts.

"Essential mineral nutrients" are understood to be nitrogen compounds, in particular nitrates, nitrites, ammonia, ammonium compounds and/or urea; phosphorus compounds, in particular phosphates and/or phosphites; sulphur compounds, in particular sulfates; and potassium, magnesium, calcium, or iron compounds and compounds of trace elements, in particular boric acid, cobalt sulfate, copper sulfate and/or zinc sulfate. In one embodiment, essential mineral nutrients comprise in situ mineralisable organic phosphorus and sulphur compounds, preferably phosphonates and/or methylsulphonylmethane.

According to the invention, "mixotrophic cultivation" is understood to be simultaneous phototrophic and heterotrophic cultivation.

"Phototrophic cultivation" is understood to be cultivation in the presence of essential mineral nutrients, carbon dioxide and light.

"Microalgae" are understood to be microscopic, eukaryotic organisms that live in water and perform photosynthesis. Microscopic organisms are understood to be organisms with a maximum length of 1 mm.

According to the invention, the ability of different microalgae to simultaneously generate phototrophic and heterotrophic growth is utilised. In one embodiment of the method, cultivation of heterotrophic microalgae takes place, preferably chlorophytes, in particular *Chlorella, Scenedesmus, Muriellopsis, Tetraselmis*, particularly preferably *Chlorella vulgaris, Chlorella sorokiniana, Chlorella regularis, Chlorella zofingiensis, Chlorella protothecoides, Parachlorella kessleri* or *Scenedsmus vakuolatus*; or diatoms, in particular *Odontella aurita* or *Phaeodactylum trikornutum*; or *Euglena* species, in particular *Euglena gracilis*; or Haptophyta, preferably *Isochrysis* species or *Pavlova* species. A "heterotrophic microalga" is understood to be a microalga that grows organic biomass in the presence of organic substrates, essential mineral nutrients and oxygen even in the absence of light.

An "inoculum" is understood to be microalgae cells for inoculating a culture medium in a device, preferably a first culture medium containing microalgae cells for inoculating a second culture medium in a device. "Inoculation" is understood to be the addition of an object capable of replication, in particular a cell, to a culture medium. "Inoculation" is preferably understood to be adding a first culture medium containing a cell to a second culture medium.

A "culture medium" is understood to be an aqueous solution for the cultivation of microalgae. In one embodiment, the culture medium is an aqueous buffer solution. In a preferred embodiment, the culture medium comprises organic substrates and/or essential mineral nutrients.

In one embodiment of the method, the inoculation of a culture medium with the inoculum in step a) comprises individual subcultivation steps with increasing culture volumes, preferably three subcultivation steps, with a dilution with culture medium having a dilution factor of 10 being particularly preferred in each case.

In one embodiment of the method, the individual subcultivation steps take place under the same conditions, preferably with the same culture medium as the cultivation of the at least one microalgae strain in a first device under heterotrophic culture conditions in step b).

In one embodiment of the method, the culture medium, after the inoculation in step a), is transferred to the first device for cultivating the at least one microalgae strain under heterotrophic culture conditions in step b).

In one embodiment of the method, an organic substrate is added in a clocked or continuous manner in the cultivation of the at least one microalgae strain in a first device under heterotrophic culture conditions in step b).

In one embodiment of the method, the at least one microalgae strain is cultivated in a first device under heterotrophic culture conditions in step b) with stirring, preferably at a stirring speed of 10 rpm to 1000 rpm.

Advantageously, the introduction of the process gas at the lower end of the second device and the at least partial compression or at least partial condensation of the process gas result in the formation of gas bubbles which flow through the second device, as a result of which thin layers are produced in the microalgae culture between the wall of the second device and gas bubbles. Also advantageously, the thin layers ensure that the microalgae are adequately supplied with light.

In one embodiment of the method, the process gas in step c) is air or a carbon dioxide-enriched air mixture, preferably an exhaust gas from heterotrophic cultivation from the first device or produced from technical gases. In one embodiment, the composition and amount of the introduced process gas in step c) are adapted to the process sequence.

"Air" is understood to be a gas mixture comprising nitrogen and oxygen and, in small amounts, preferably less than 0.1 vol. %, carbon dioxide. A "carbon dioxide-enriched air mixture" is understood to be a gas mixture comprising nitrogen, oxygen and carbon dioxide having a carbon dioxide content of 0.1 vol. % to 20 vol. %.

In one embodiment of the method, a further process gas is introduced into the first device in step b), the further process gas preferably being an oxygen-containing gas or gas mixture. An "oxygen-containing gas or gas mixture" is understood to be a gas or gas mixture containing oxygen in a proportion of 21 vol. % to 100 vol. %.

In a preferred embodiment of the method, the composition and amount of the introduced oxygen-containing gas or gas mixture in step b) are adapted to the process sequence.

In one embodiment of the method, the process gas is introduced in a clocked or continuous manner. "Clocked" is understood to mean the introduction of the process gas in the form of successive, separated gas bubbles. The process gas is preferably introduced in a clocked manner with an injection time of 0.1 s to 10 s, with 0.5 to 50 injections per minute.

In one embodiment of the method, the amount of process gas introduced is 1 $cm^3$/s to 100,000 $cm^3$/s, preferably 1 $cm^3$/s to 10,000 $cm^3$/s, particularly preferably 10 $cm^3$/s to 1,000 $cm^3$/s.

In one embodiment of the method, the pressure of the introduced process gas is 0.3 bar to 5 bar above the hydrostatic pressure of the first and second devices, preferably 0.5 to 2.5 bar above the hydrostatic pressure of the first and second devices, particularly preferably 0.5 to 1.5 bar above the hydrostatic pressure of the first and second devices.

In one embodiment of the method, the system pressure of the first device and second device is identical.

In further embodiments of the method, at least a portion of the at least one microalgae strain is conveyed in a clocked or continuous manner from the first device in step b) into the second device in step c) and/or from the second device in step c) into the first device in step b).

In preferred embodiments of the method, at least a portion of the at least one microalgae strain is conveyed in a clocked or continuous manner from the first device in step b) into the second device in step c) and from the second device in step c) into the first device in step b).

In a particularly preferred embodiment, the dwell time of the portion of the at least one microalgae strain in the second device is between 60 s and 3600 s.

The clocked or continuous conveying is preferably carried out by introducing a process gas in step c) or by a pump or by introducing a process gas in step c) and a pump.

In one embodiment of the method, the volume of the clocked or continuously conveyed portion of the at least one microalgae strain from the first device in step b) to the second device in step c) and/or from the second device in step c) to the first device in step b) is twice to ten times the filling volume of the second device per hour, preferably four times the filling volume of the second device per hour. The filling volume is understood to be the volume of the at least one microalgae strain in culture medium in a device.

In one embodiment of the method, the temperature of the at least one microalgae strain in culture medium in the first device and/or in the second device is in the range from 10° C. to 40° C. In a further embodiment, the difference in temperatures of the at least one microalgae strain in culture medium in the first device and in the second device is 1 K to 10 K.

In one embodiment of the method, the pH of the at least one microalgae strain in culture medium in the first device and/or in the second device is in the range from pH 5.5 to pH 9.5, preferably in the range of from pH 6.0 to pH 8.5, particularly preferably in the range of from pH 6.5 to pH 7.5.

In further embodiments, the method according to the invention comprises at least one further step, the further step being selected from phototrophic cultivation, mixotrophic cultivation, harvesting the biomass and/or drying the harvested biomass. "Harvesting the biomass" is understood to mean the separation of the microalgae from the culture medium.

The invention also relates to a system for the simultaneous heterotrophic and mixotrophic cultivation of microalgae, comprising
i. a first device, the first device being designed for heterotrophic cultivation,
ii. a second device comprising a tube made of translucent material and at least one light source, the second device being designed for mixotrophic cultivation,
iii. a first connecting element for connecting the first device to the second device,
wherein the first connecting element connects the bottom of the first device to the inlet of the second device,
iv. a second connecting element for connecting the first device to the second device,
wherein the second connecting element connects the upper part of the first device to the outlet of the second device,
wherein the second device comprises an injector for introducing a process gas at the lower end or the first connecting element.

The inlet of the second device is understood to be the lower end of the second device and the outlet of the second device is understood to be the upper end of the second device.

In one embodiment, the system according to the invention is a closed system. A closed system advantageously reduces the risk of contamination. A higher process-gas pressure is also advantageously achieved. Evaporation of the culture medium is also advantageously prevented. Higher biomass densities in the culture suspension are also advantageously achieved.

The first device, designed for heterotrophic cultivation, is preferably a closed stirred tank which can be operated under sterile conditions, particularly preferably with a ratio of diameter to height in the range of from 1:1 to 1:3.

In one embodiment, the first device is a fermenter, preferably a temperature-controllable, pH-controllable and/or process gas supply-controllable fermenter. In one embodiment, the fermenter comprises a stirring apparatus, preferably an agitator, particularly preferably a Rushton turbine agitator, and/or an injector for introducing a process gas.

The tube made of translucent material is preferably a flow tube. A flow tube is understood to be a tube which enables clocked or continuous conveying of microalgae, in particular clocked or continuous conveying of a portion of at least one microalgae strain with a volume in the range from twice to ten times the filling volume of the tube made of translucent material per hour, preferably four times the filling volume of the tube made of translucent material per hour.

In one embodiment, the tube made of translucent material is a collector unit of a photobioreactor. A collector unit of a photobioreactor is understood to be the part of a photobioreactor which has light entry surfaces.

The system for the simultaneous heterotrophic and mixotrophic cultivation of microalgae preferably has a ratio of the volume of the first device to the volume of the tube made of translucent material in the range from 10:1 to 1:5.

In one embodiment of the system, the tube consisting of translucent material is arranged so as to ascend in a spiral shape around a support frame in the form of a truncated cone or a hollow cylinder, the support frame comprising at least one light source.

In one embodiment of the system, the second device comprises at least one further light source for irradiating the tube made of translucent material from the outside, the at least one further light source preferably being a surface spotlight.

In one embodiment of the system, the translucent material is selected from glass or transparent polymers, preferably silicones, polyvinyl chloride (PVC), polyacrylates, polyethylene or borosilicate glass.

In one embodiment of the system, the tube made of translucent material comprises at least one further material selected from UVB- and UVC-permeable materials, preferably quartz glass.

In one embodiment of the system, the at least one light source is selected from a sodium vapour lamp or an LED spotlight.

In a preferred embodiment of the system, the at least one light source has a wavelength in the range of from 400 nm to 520 nm or from 600 nm to 720 nm.

In one embodiment of the system, the at least one light source has a light output in the range from 1 $W/m^2$ to 150 $W/m^2$.

In one embodiment of the system, the second device comprises at least one further light source, the at least one further light source having a wavelength in the range of from 280 nm to 320 nm.

In one embodiment of the system, the first device and/or the second device can be sterilised. In one embodiment of the system, the first connecting element and/or the second connecting element can be sterilised, and are preferably a sterilisable flange.

In one embodiment of the system, the second device comprises a pump, preferably a rotary lobe pump. The pump is preferably arranged downstream of the first connecting element.

Another aspect of the invention relates to the use of the method according to the invention or the system according to the invention for the cultivation of microalgae.

In order to implement the invention, it is also expedient to combine the above-described embodiments and features of the claims.

BRIEF DESCRIPTION OF THE DRAWINGS

The invention will be explained in greater detail in the following with reference to some embodiments and accompanying drawings. The embodiments are intended to describe the invention without having a limiting effect thereon.

FIG. 1 shows a schematic view of the system according to the invention for the simultaneous heterotrophic and mixotrophic cultivation of microalgae comprising a first device 1 and a second device 2 comprising a tube made of translucent material.

DETAILED DESCRIPTION OF THE PREFERRED EMBODIMENTS

The first device 1 is designed for heterotrophic cultivation and is preferably a closed stirred tank which can be operated under sterile conditions. The first device 1 preferably comprises an injector for introducing a process gas 5 and an agitator 6, particularly preferably a Rushton turbine agitator. In the bottom region of the first device 1, there is a first connecting element 3 for the leak-tight connection of the first device 1 to the second device 2. The second device 1 preferably comprises a pump 7, particularly preferably a sterilisable rotary lobe pump. The pump 7 is connected to the tube made of translucent material, an injector for introducing a process gas 10 for the mixotrophic cultivation being located between the pump 7 and the tube made of translucent material. The tube made of translucent material is arranged so as to ascend around a support frame (not shown). The first light source 8 enables illumination from the inside and the second light source 9 enables illumination from the outside. The outlet or the upper end of the tube made of translucent material is connected in a pressure-tight manner to the upper part of the first device 1 via a second connecting element 4.

Embodiment 1

*Chlorella sorokiniana* is cultivated in an installation according to the invention in accordance with FIG. 1. The first device 1 and the second device 2 each have a working volume of 400 l.

The system is filled with 600 l of culture medium I and sterilised. The culture medium I is composed as follows: 1.5 g/l $KNO_3$; 50 mg/l $KH_2PO_4$; 100 mg/l $MgSO_4 \cdot 7H_2O$; 14 mg/l $FeSO_4 \cdot 7H_2O$; 1 mg/l $MnSO_4 \cdot 5H_2O$; 0.7 mg $ZnSO_4 \cdot 7H_2O$; 0.06 mg/l $H_3BO_3^-$; 0.024 mg/l $CoSO_4 \cdot 7H_2O$; 0.024 mg/l $CuSO_4 \cdot 5H_2O$; 0.01 mg/l $(NH_4)_6Mo_7O_{24} \cdot 4H_2O$ and 10 g/l glucose, the glucose being sterilised separately and only being added after the medium has been sterilised. The culture medium is inoculated with 30 l of inoculum containing approx. 20 g/l of *Chlorella sorokiniana* via the first device 1 and is continuously pumped into the second device 2 with stirring in the first device 1 and from there back into the first device 1. The second device 2 is illuminated with light in the PAR (photosynthetically active radiation) range at an intensity of 80 W/m², based on the inner surface of the second device, which is regarded as a truncated cone. Both devices are temperature-controlled to 32° C. and the pH is automatically adjusted to pH 6.8 with sulphuric acid ($H_2SO_4$). The *Chlorella sorokiniana* microalgae are cultivated for 4 days, and the required glucose and minerals are supplied discontinuously according to the consumption generated by the algae growth. The amount and composition of the supplied process gases, in particular the carbon dioxide-enriched gas mixture and the oxygen-containing gas mixture, are regulated separately in the first device 1 and the second device 2 in accordance with the algae growth. After 4 days, the biomass in the installation has reached a concentration of 35 g/l. The biomass is harvested, enriched to 100 g/l using a centrifuge and spray-dried. The biomass has a chlorophyll content of 3.0% and contains 3500 ppm lutein based on the dry matter.

Embodiment 2

*Chlorella sorokiniana* is cultivated in an installation according to the invention in accordance with FIG. 1. The first device 1 has a working volume of 100 l and the second device 2 has a working volume of 400 l.

The system is sterilised and filled with 450 l culture medium II. The culture medium II is composed as follows: 0.5 g/l $KNO_3$; 1 g/l urea; 100 mg/l $KH_2PO_3$; 100 mg/l $MgSO_4 \cdot 7H_2O$; 14 mg/l $FeSO_4 \cdot 7H_2O$; 1 mg/l $MnSO_4 \cdot 5H_2O$; 0.7 mg $ZnSO_4 \cdot 7H_2O$; 0.06 mg/l $H_3BO_3^-$; 0.024 mg/l $CoSO_4 \cdot 7H_2O$; 0.024 mg/l $CuSO_4 \cdot 5H_2O$; 0.01 mg/l $(NH_4)_6Mo_7O_{24} \cdot 4H_2O$ and 0.5 g/l sodium acetate.

The culture medium is inoculated with 5 l of inoculum containing approx. 100 g/l of *Chlorella sorokiniana* via the first device 1. Before the inoculation, 5 g of sodium acetate is added to the inoculum, the pH is lowered to pH 3.2 with $H_2SO_4$ over a period of 30 minutes and then raised to pH 7.0 with a sodium hydroxide (NaOH) solution. With stirring, the microalgae strain and the culture medium from the first device 1 are continuously pumped into the second device 2 and from there back into the first device 1. The second device 2 is illuminated with light in the PAR range with an intensity of 70 W/m², based on the inner surface of the second device, which is regarded as a truncated cone. Both devices are temperature-controlled to 30° C. and the pH is automatically adjusted to pH 7.0 with acetic acid. The acetic acid required for the carbon supply is added discontinuously in a pH-controlled manner in accordance with the consumption generated by the algae growth. With the addition of acetic acid, the necessary nitrogen in the form of ammonium acetate and the trace elements iron and manganese are also added. $KH_2PO_4$ is dosed separately in accordance with the consumption generated by the algae growth. The amount and composition of the supplied process gases, in particular the carbon dioxide-enriched gas mixture and the oxygen-containing gas mixture, are regulated separately in the first device 1 and the second device 2 in accordance with the algae growth. After 8 days, the biomass in the installation has reached a concentration of 12 g/l. The biomass is harvested, enriched to 100 g/l using a centrifuge and spray-dried. The biomass has a chlorophyll content of 3.5% and contains 4000 ppm lutein based on the dry matter.

Embodiment 3

*Chlorella sorokiniana* is cultivated in an installation according to the invention in accordance with FIG. 1 in the form of a revolving method. The first device 1 has a working volume of 100 l and the second device 2 has a working volume of 400 l. The system is sterilised and filled with 450 l culture medium II. The culture medium II is composed as follows: 0.5 g/l $KNO_3$; 1 g/l urea; 100 mg/l $KH_2PO_3$; 100 mg/l $MgSO_4 \cdot 7H_2O$; 14 mg/l $FeSO_4 \cdot 7H_2O$; 1 mg/l $MnSO_4 \cdot 5H_2O$; 0.7 mg $ZnSO_4 \cdot 7H_2O$; 0.06 mg/l $H_3BO_3^-$; 0.024 mg/l $CoSO_4 \cdot 7H_2O$; 0.024 mg/l $CuSO_4 \cdot 5H_2O$; 0.01 mg/l $(NH_4)_6Mo_7O_{24} \cdot 4H_2O$ and 0.5 g/l sodium acetate.

The culture medium is inoculated with 5 l of inoculum containing approx. 100 g/l of *Chlorella sorokiniana* via the first device 1. Before the inoculation, 5 g of sodium acetate is added to the inoculum, the pH is lowered to pH 3.2 with $H_2SO_4$ over a period of 30 minutes and then raised to pH 7.0 with an NaOH solution. With stirring, the microalgae strain and the culture medium from the first device 1 are continuously pumped into the second device 2 and from there back into the first device 1. The second device 2 is illuminated with light in the PAR range with an intensity of 70 W/m², based on the inner surface of the second device, which is regarded as a truncated cone. Both devices are temperature-controlled to 30° C. and the pH is automatically adjusted to pH 7.0 with acetic acid. The acetic acid required for the carbon supply is added discontinuously in a pH-controlled manner in accordance with the consumption generated by the algae growth. With the addition of acetic acid, the necessary nitrogen in the form of ammonium acetate and the trace elements iron and manganese are also added. $KH_2PO_4$ is dosed separately in accordance with the consumption generated by the algae growth. The amount and composition of the supplied process gases, in particular the carbon dioxide-enriched gas mixture and the oxygen-containing gas mixture, are regulated separately in the first device 1 and the second device 2 in accordance with the algae growth. After 8 days, the biomass in the installation has reached a concentration of 12 g/l. The biomass is harvested, enriched to 100 g/l using a centrifuge and spray-dried. The biomass has a chlorophyll content of 3.5% and contains 4000 ppm lutein based on the dry matter.

Before the inoculation, 5 g of sodium acetate is added to 5 l of the harvested and enriched biomass, the pH is lowered to pH 3.2 with $H_2SO_4$ over a period of 30 minutes and then raised to pH 7.0 with a sodium hydroxide (NaOH) solution. With this biomass, the system that has been refilled with culture medium II after the total harvest is inoculated without further intermediate disinfection. The cultivation is continued with the above-described method steps after the inoculation. The harvested biomass has a chlorophyll content of 3.5% and contains 4000 ppm lutein based on the dry matter.

Embodiment 4

12 l of a 10% *Chlorella sorokiniana* suspension obtained in accordance with embodiment 1 are used to inoculate a tubular photobioreactor filled with 1200 l of culture medium III. Culture medium III corresponds to culture medium I, but does not contain glucose. The microalgae culture is cultivated in the photobioreactor over a period of 4 weeks. The cultivation takes place in the natural diurnal rhythm, and a minimum light intensity in the PAR range of 80 W/m² is set by additional lighting that can be switched on in the day phase, based on the inner surface of the second device, which is regarded as a truncated cone. The pH is automatically regulated by introducing carbon dioxide ($CO_2$). Mineral nutrients and trace elements are dosed in accordance with the consumption generated by the algae growth. After 5 days, the biomass in the installation has reached a concentration of 3.5 g/l.

400 l of culture suspension is harvested and replaced with fresh culture medium III. This process is repeated until the end of week 4, the last harvest cycle is designed to be a total harvest.

Embodiment 5

In an alternative configuration of embodiment 1, *Chlorella zofingiensis* is cultivated in an installation according to the invention in accordance with FIG. 1, with both devices being temperature-controlled to 28° C.

12 l of the accordingly obtained 10% *Chlorella zofingiensis* suspension are used to inoculate a tubular photobioreactor filled with 1200 l of culture medium III. Culture medium III corresponds to culture medium I, but does not contain glucose. The microalgae culture is cultivated in the photobioreactor over a period of 4 weeks at 28° C. daytime temperature and 20° C. night temperature. The cultivation takes place in the natural diurnal rhythm, and a minimum light intensity in the PAR range of 80 W/m² is set by additional lighting that can be switched on in the day phase, based on the inner surface of the second device, which is regarded as a truncated cone. The pH is automatically regulated by introducing carbon dioxide ($CO_2$). Mineral nutrients and trace elements are dosed in accordance with the consumption generated by the algae growth. After 5 days, the biomass in the installation has reached a concentration of 3.0 g/l. 400 l of culture suspension is harvested and replaced with fresh culture medium III. This process is repeated until the end of week 4, the last harvest cycle is designed to be a total harvest. The biomass harvested in each case contains, in addition to other carotenoids, 1300 ppm astaxanthin, based on the dry matter.

Embodiment 6

*Chlorella vulgaris* is cultivated in an installation according to the invention in accordance with FIG. 1, with an area of 50 cm of the tube made of translucent material in the second device 2 having been replaced with a separately illuminated tube made of quartz glass. The first device 1 has a working volume of 100 l and the second device 2 has a working volume of 400 l.

The system is sterilised and filled with 450 l culture medium II. The culture medium II is composed as follows: 0.5 g/l $KNO_3$; 1 g/l urea; 100 mg/l $KH_2PO_3$; 100 mg/l $MgSO_4 \cdot 7H_2O$; 14 mg/l $FeSO_4 \cdot 7H_2O$; 1 mg/l $MnSO_4 \cdot 5H_2O$; 0.7 mg $ZnSO_4 \cdot 7H_2O$; 0.06 mg/l $H_3BO_3^-$; 0.024 mg/l $CoSO_4 \cdot 7H_2O$; 0.024 mg/l $CuSO_4 \cdot 5H_2O$; 0.01 mg/l $(NH_4)_6Mo_7O_{24} \cdot 4H_2O$ and 0.5 g/l sodium acetate.

The culture medium is inoculated with 5 l of inoculum containing approx. 100 g/l of *Chlorella vulgaris* via the first device 1. Before the inoculation, 5 g of sodium acetate is added to the inoculum, the pH is lowered to pH 3.2 with $H_2SO_4$ over a period of 30 minutes and then raised to pH 7.0 with an NaOH solution. With stirring, the microalgae strain and the culture medium from the first device 1 are continuously pumped into the second device 2 and from there back into the first device 1. The second device 2 is illuminated with light in the PAR range with an intensity of 70 W/m², based on the inner surface of the second device, which is regarded as a truncated cone. The portion of the tube made of quartz glass is exposed to UVB radiation. Both devices are temperature-controlled to 27° C. and the pH is automatically adjusted to pH 7.0 with acetic acid. The acetic acid required for the carbon supply is added discontinuously in a pH-controlled manner in accordance with the consumption generated by the algae growth. With the addition of acetic acid, the necessary nitrogen in the form of ammonium acetate and the trace elements iron and manganese are also added. $KH_2PO_4$ is dosed separately in accordance with the consumption generated by the algae growth. The amount and composition of the supplied process gases, in particular the carbon dioxide-enriched gas mixture and the oxygen-containing gas mixture, are regulated separately in the first device 1 and the second device 2 in accordance with the algae growth. After 8 days, the biomass in the installation has reached a concentration of 8 g/l. The biomass is harvested, enriched to 100 g/l using a centrifuge and spray-dried. The biomass has a chlorophyll content of 3.5% and contains, in addition to carotenoids, 0.05 ppm vitamin D2 based on the dry matter.

LIST OF REFERENCE NUMERALS 1 first device, preferably a closed stirred tank which can be operated under sterile conditions
2 second device comprising a tube made of translucent material
3 first connecting element
4 second connecting element
5 injector for introducing a process gas
6 agitator
7 pump
8 first light source
9 second light source
10 injector for introducing a process gas

The invention claimed is:
1. A method for the simultaneous heterotrophic and mixotrophic cultivation of microalgae, comprising the steps of:

a) providing an inoculum comprising at least one microalgae strain and inoculating a culture medium with the inoculum,
b) cultivating the at least one microalgae strain in a first device under heterotrophic culture conditions in a culture medium that comprises an organic carbon source,
c) cultivating the at least one microalgae strain in a second device under mixotrophic culture conditions in a culture medium that comprises an organic carbon source,
wherein at least a portion of the at least one microalgae strain is conveyed from the first device in step b) to the second device in step c) and/or from the second device in step c) to the first device in step b),
wherein a process gas is introduced at the lower end of the second device,
wherein the process gas is introduced so as to be at least partially compressed or at least partially condensed,
wherein at least a portion of the at least one microalgae strain is conveyed in a continuous or clocked manner from the first device in step b) to the second device in step c) and/or from the second device in step c) to the first device in step b), by introducing a process gas in step c), and
wherein during said method, heterotrophic and mixotrophic cultivation of microalgae are performed simultaneously.

2. The method according to claim 1, wherein the process gas in step c) is air or a carbon dioxide-enriched air mixture.

3. The method according to claim 1, wherein the process gas is introduced in a continuous or clocked manner.

4. The method according to claim 1, wherein the amount of process gas introduced is 1 $cm^3/s$ to 100,000 $cm^3/s$.

5. The method according to claim 1, wherein at least a portion of the at least one microalgae strain is conveyed in a continuous or clocked manner from the first device in step b) to the second device in step c) and/or from the second device in step c) to the first device in step b).

6. The method according to claim 1, wherein the method comprises at least one further step, the further step being selected from phototrophic cultivation, mixotrophic cultivation, harvesting the biomass and/or drying the harvested biomass.

7. The method according to claim 2, wherein the process gas in step c) is an exhaust gas from a heterotrophic cultivation from the first device.

8. The method according to claim 2, wherein the process gas in step c) is produced from technical gases.

9. The method according to claim 4, wherein the amount of process gas introduced is 1 $cm^3/s$ to 10,000 $cm^3/s$.

10. The method according to claim 4, wherein the amount of process gas introduced is 10 $cm^3/s$ to 1,000 $cm^3/s$.

11. The method according to claim 1, wherein at least a portion of the at least one microalgae strain is conveyed in a continuous or clocked manner from the first device in step b) to the second device in step c) and/or from the second device in step c) to the first device in step b), by means of a pump.

12. The method according to claim 1, wherein introduction of the process gas at the lower end of the second device and the at least partial compression or at least partial condensation of the process gas result in the formation of gas bubbles which flow through the second device, as a result of which thin layers are produced in the microalgae culture between the wall of the second device and gas bubbles.

13. The method according to claim 2, wherein the process gas is introduced in a continuous or clocked manner.

14. The method according to claim 2, wherein the amount of process gas introduced is 1 $cm^3/s$ to 100,000 $cm^3/s$.

15. The method according to claim 2, wherein the amount of process gas introduced is 10 $cm^3/s$ to 1,000 $cm^3/s$.

16. The method according to claim 3, wherein the amount of process gas introduced is 1 $cm^3/s$ to 100,000 $cm^3/s$.

17. The method according to claim 3, wherein the amount of process gas introduced is 10 $cm^3/s$ to 1,000 $cm^3/s$.

18. The method according to claim 12, wherein:
the process gas in step c) is air or a carbon dioxide-enriched air mixture;
the process gas is introduced in a continuous or clocked manner; and
the amount of process gas introduced is 1 $cm^3/s$ to 100,000 $cm^3/s$.

19. The method according to claim 18, wherein the amount of process gas introduced is 10 $cm^3/s$ to 1,000 $cm^3/s$.

* * * * *